United States Patent [19]

Pettit

[11] 4,388,457
[45] Jun. 14, 1983

[54] PHYLLANTHOSTATIN COMPOUNDS

[75] Inventor: George R. Pettit, Paradise Valley, Ariz.

[73] Assignee: University Patents, Inc., Norwalk, Conn.

[21] Appl. No.: 348,114

[22] Filed: Feb. 11, 1982

[51] Int. Cl.³ .................. C07H 7/06; C07H 13/00; A61K 31/71
[52] U.S. Cl. .................. 536/4.1; 424/180; 424/181; 536/18.1
[58] Field of Search .......... 536/4, 115, 4.1, 18.1; 424/180

[56] References Cited

U.S. PATENT DOCUMENTS 3,954,881  5/1976  Bowler ........................ 536/4
4,316,983  2/1982  Bollag et al. ................. 536/4

OTHER PUBLICATIONS

Watt, J. M. et al., The Medicinal and Poisonous Plants of Southern and Eastern Africa; E. S. Livingstone, Ltd., London, 2nd Ed., 1962, p. 426.
Morton, J. F., "Major Medicinal Plants," C. C. Thomas, Springfield, Ill., 1977, pp. 193, 366.
Hartwell, J. L., Lloydia, 32, 157 (1969).
Spjut, R. W. et al., Cancer Treatment Reports, 60, 979 (1976).
Kupchan, S. M., et al., J. Am. Chem. Soc., 99, 3199 (1977).
Kupchan et al., "Jour. of the Amer. Chem. Soc.", vol. 99, No. 9, Apr. 27, 1977, pp. 3199-3201.
Kupchan et al., "Chem. Abst.", vol. 87, 1977, p 5779s.

Primary Examiner—Johnnie R. Brown
Attorney, Agent, or Firm—Roman Saliwanchik

[57] ABSTRACT

New antineoplastic glycosides, phyllanthostatin 1, 2 and 3, and the related glycoside, phyllanthoside, have been isolated from the Central American tree, *Phyllanthus acuminatus* Vahl. These compounds exhibit activity against the National Cancer Institute's P388 lymphocytic leukemia. Also, phyllanthoside was found to possess a curative level of activity against the murine B16 malanoma.

3 Claims, No Drawings

PHYLLANTHOSTATIN COMPOUNDS

Financial assistance was provided by Contract NO1-CM-97297 with the Division of Cancer Treatment, NCI, National Institutes of Health, DHW, Grant Nos. CA16049-06 and 07, awarded by the National Cancer Institute, DHW, Mrs. Mary Dell Pritzlaff, the Ol in Foundation, (Spencer T. and Ann W.), the Fannie E. Rippel Foundation, and the National Science Foundation Regional Facility at the University of South Carolina (CH78-18723).

BACKGROUND OF THE INVENTION

The Euphorbiaceae family is rich in plants with a long history of human medicinal applications [Watt, J. M. and M. G. Breyer-Brandwijk, "The Medicinal and Poisonous Plants of Sourthern and Eastern Africa," 2nd Ed., E. S. Livingstone Ltd., London, 1962, p. 426] [Morton, J. F., "Major Medicinal Plants," C. C. Thomas, Springfield, Ill., 1977, pp. 193, 366]. The Euphorbiaceae genus Phyllanthus contains about 600 species ranging from free floating aquatic forms to trees, including several species that have been employed in the primitive treatment of cancer [Hartwell, J. L., Lloydia, 32, 157 (1969)] [Spjut, R. W. and R. E. Perdue, Cancer Treatment Reports, 60, 979 (1976)]. Because of the U.S. National Cancer Institute's (NCI) exploratory plant evaluation program, in collaboration with the U.S. Department of Agriculture (USDA), the roots of a tree believed at the time to be P. brasiliensis Muell were collected about a decade ago in Costa Rica. An ethanol extract of the original collection was found to inhibit growth of the NCI murine P388 lymphocytic leukemia (PS) system, and the Kupchan group [Kupchan, S. M., E. J. LaVoie, A. R. Brankfman, B. Y. Fei, W. M. Bright and R. F. Bryan, J. Am. Chem. Soc., 99, 3199 (1977)] isolated and partially characterized a PS active glycoside termed phyllanthoside from a 1974 recollection. It is now believed that the roots from which Kupchan et al. isolated phyllanthoside came from P. acuminatus Vahl rather than P. brasiliensis.

BRIEF SUMMARY OF THE INVENTION

A novel extraction and purification process was developed to obtain the known antitumor substance phyllanthoside and the novel antitumor substances phyllanthostatins 1, 2 and 3 from roots of the tropical plant, Phyllanthus acuminatus Vahl. All of these compounds are highly active in the p388 murine lymphocytic leukemia test system giving increases in life span of 40-50% at doses of 7-80 mg/kg. Phyllanthoside and phyllanthostatin 1 were also active in the B16 murine melanoma system giving increases in life span of 90 and 105%, respectively, at doses of 16 and 24 mg/kg, respectively.

DETAILED DESCRIPTION OF THE INVENTION

The Organism

Description:
Phyllanthus acuminatus Vahl is a deciduous, monoecious, arborescent shrub or small tree, sparsely or much-branched from 2-8 meters high. Branchlets are notably green and angulate, bipinnatiform. Leaves alternate, membranous, ovate to broadly elliptical, abruptly cupsidate-acuminate, scabridous above, 2-2.5 cm. long and 1-2.5 cm. broad, on petioles 1.5-3 mm. long. Stipules deltoid, blunt, up to 1.3 mm. long, persistent and often reflexed. Flowers are in axially clusters, usually only one pistillate among several male flowers; the male on capillary pedicels 1-4.5 mm. long, with three connate filaments and three "free" glands in two circles that are opposite the three outer sepals, with anthers dehising by oblique slits; the female on slender, angled pedicles 5-9 mm. long and elongating to 15 mm. in fruit, with bifid styles. Calyx lobes 6, green with whitish margins. Capsule subglobose, 3.5-5 mm., reticulate veiny. Seeds are smooth, reddish brown, 2-2.5 mm. long.

Geographical Distribution and Ecology:
Widespread in Latin America; from southern Mexico (including Baja California Sur), West Indies, Central and South America to Peru and northern Argentina. Brushy or forested slopes, mostly in the lowlands. Reaching the fringes of the deserts where confined to arroyos.

Isolation and Purification

Roots of P. acuminatus were processed by a convenient new technique for initial plant and animal extraction [Arene, E. O., G. R. Pettit, and R. H. Ode, Lloydia, 41, 186 (1978) and Pettit, G. R., Y. Fujii, J. A. Hasler, J. M. Schmidt and C. Michel, J. Nat. Prod., In Press].

The NCI PS in vivo and in vitro lymphocytic leukemia bioassays were employed to guide each step of the subsequent separation [Schmidt, J. M. and G. R. Pettit, Experientia, 34 659 (1978)].

The structures of the compounds of this invention can be found depicted in the Chart.

Extraction, Partition and Chromatography:
The chipped roots (81 kg) were extracted with methanol-methylene chloride (1/1; 120 l) at ambient temperature for 14 days. Addition of water (25% by volume) separated the methylene chloride phase which was concentrated under vacuo to give the first methylene chloride extract (192 g). The aqueous methanol phase was adjusted by addition of further methanol and methylene chloride in the ratio aqueous phase-methanol-methylene chloride (4:1.2:1.8) and the plant material was further extracted with this mixture for seven days. Addition of water (15% by volume) separated the methylene chloride phase which was concentrated as before to give the second methylene chloride extract (283 g). The combined methylene chloride extracts (475 g) were partitioned between aqueous methanol (1/9; 3 l) and hexane (1×2 l and 3×1 l) to give an inactive hexane soluble fraction (170 g) and insoluble material (17 g: Fraction A). The aqueous methanol fraction was diluted ¼ and extracted with carbon tetrachloride (8×1 l) to give a PS-active carbon tetrachloride soluble fraction (44 g). After further dilution of the aqueous methanol fraction to ⅔, it was extracted with methylene chloride (7×1.5 l) to give a PS-active methylene chloride soluble fraction (120 g). Treatment of the active carbon tetrachloride soluble fraction (44 g) with methanol (100 ml) gave insoluble material (4.7 g; Fraction B) and a soluble fraction which was combined with a solution of the active methylene chloride soluble fraction (210 g) in methanol (700 ml). Half of this solution was applied to a column of Sephadex LH-20 (2 kg; 105×10 cm) and elution with methanol between volumes 5100-6100 ml gave an active fraction (55 g). Two 10 g portions of this fraction were separately chromatographed on Sephadex LH20 (700 g; 220×4 cm) using methanol-methylene chloride (3/2) as eluant. Elution between volumes 1450–1700 ml gave an active fraction (7.5 g). Chromatography of this fraction (13 g) on silica gel-60 (825 g; 84×5 cm) using chloroform-methanol-water (70/7/0.5) as eluant gave the following active fractions (weight; elution volumes): Fraction C (0.90 g; 1–1320 ml); Fraction D (2.9 g; 1321–1975 ml); Fraction E (2.1 g; 2200–2880 ml); Fraction F (2.75 g; 2880–4500 ml).

The carbon tetrachloride (44 g) and methylene chloride (210 g) fractions were combined and chromatographed on Sephadex LH-20, eluting with methanol. A portion of the eluate from the Sephadex column was repeatedly chromatographed on a silica gel column. Elution between volumes 1530–2000 ml gave phyllanthostatin I (0.24 g) as an amorphous solid. Purity was determined by high pressure liquid chromatography (HPLC) on a $\mu$ Porasil column eluting with a mixture of methylene chloride, methanol and water (97:3:0.2). Phyllanthostatin 1 had the following characteristics: mp 125°–126° C.; FD mass spec. m/e 805 (M+ +H); $[\alpha]_D^{26}$ −3.6° (c 0.83, CHCl$_3$); $\lambda_{max}^{MeOH}$ (log $\epsilon$) 216 (4.19), 222 (4.12) and 277 (4.29); nm; IR (KBr) $\nu_{max}$ 3450, 1755, 1740, 1710, 1640, 1452, 1380, 1310, 1245, 1170, 1075 and 770 cm$^{-1}$. Additional PS active fraction (Fraction D, 2.9 g) was chromatographed on silica gel-60 (Lobos C column); development of the column with chloroform (600 ml), 1%—(500 ml), 2%—(500 ml) and 3% methanol-chloroform (350 ml), followed by elution with 3% methanol-chloroform between volumes 350–620 ml gave material (2.49 g) which was further chromatographed on silica gel-60 (3 Lobos B columns) using methylene chloride-methanol-water (97/3.0/0.1) as eluant. Elution between volumes 990–1340 ml gave phyllanthoside (0.60 g) as an amorphous solid with the following characteristics: mp 125°–127° C.; FD mass spec. m/e 805 (M+ +H); $[\alpha]_D^{22}$ +16.9° (C=0.71, CHCl$_3$); $\lambda_{max}^{MeOH}$ nm (log $\epsilon$) 216 (4.25), 222 (4.19) and 277 (4.34); IR (KBr) $\nu_{max}$ 3475, 1750, 1735, 1710, 1640, 1452, 1380, 1311, 1253, 1173, 1080 and 770 cm$^{-1}$. Comparison of spectral data [Kupchan, S. M., supra] with that recorded for authentic phyllanthoside indicated that both are identical. Unfortunately, no specimens of phyllanthoside or phyllanthocin remain from Kupchan's original separations. Finally, chromatography on reverse phase (RP-2) silica (70→20%) aqueous methanol gradient) afforded 0.10 g of phyllanthostatin 2 as a colorless amorphous solid: mp 134°–136° C.; FD mass spectrum m/e 821 (M+ +H); $[\alpha]_D^{24}$ +9.33° (c 0.75, CHCl$_3$); $\lambda_{max}^{MeOH}$ nm (log $\epsilon$) 216 (4.28), 222 (4.21) and 278 (4.38); IR $\nu_{max}$ 3470, 1750, 1730, 1710, 1640, 1452, 1380, 1311, 1257, 1171, 1075 and 770 cm$^{-1}$. The chromatography was conducted as follows: The biologically active fraction (Fraction E, 2.1 g) was chromatographed on silica gel-60 (Lobos C column); development of the column with chloroform (500 ml), 1%—(500 ml), 2%—(500 ml), 3%—(800 ml) and 4% methanol-chloroform (730 ml), followed by elution with 4% methanol-chloroform between volumes 730–3430 ml gave material (1.43 g) which was further chromatographed on RP-2 silica gel-60 (100 g) using 70%—(800 ml) to 20%—aqueous methanol (800 ml) gradient elution. Elution between volumes 750–830 ml gave phyllanthostatin 2 (0.10 g) as an amorphous solid. Additional silica gel chromatography yielded 0.26 g of phyllanthostatin 3 as a colorless amorphous solid: mp 126°–130°; FD mass spectrum m/e 323 (M+ +H); $[\alpha]_D^{26}$ +15.7° (c 0.76, CHCl$_3$); $\lambda_{max}^{MeOH}$ nm (log $\epsilon$), 216 (4.25), 222 (4.18) and 278 (4.35); IR (KBr) $\nu_{max}$ 3450, 1755, 1730, 1700, 1640, 1455, 1380, 1311, 1258, 1175, 1070 and 772 cm$^{-1}$. The chromatography was conducted as follows: The biologically active fraction (Fraction F, 2.69 g) was chromatographed on silica gel-60 (Lobos C column); development with chloroform, 1%—, 2%—, 3%—(500 ml each) and 4% methanol-chloroform (650 ml), followed by elution with 4% methanol-chloroform between volumes 650–950 ml, gave material (0.88 g) which was further chromatographed on RP-2 silica gel-60 (180 g) using 60%—(900 ml) to 20% aqueous methanol (900 ml) gradient elution. Elution between volumes 350–800 ml gave material (0.45 g) which was chromatographed on silica gel-60 (3 Lobos A columns). Development with chloroform, 1%—, 2%—(150 ml each) and 3%-methanol-chloroform (100 ml) and elution with 3% methanol-chloroform between volumes 100–200 ml gave phyllanthostatin 3 (0.26 g) as an amorphous solid.

DERIVATIVES

As shown in the methods section below, phyllanthoside can be converted to phyllanthocin by methanolysis.

Phyllanthocin is then demethylated to produce the novel compound phyllanthocin acid by treating it briefly with dilute base, e.g. with 1 N NaOH at room temperature for 15 minutes. The hydrolysis reaction is stopped by neutralizing the NaOH with HCl and the phyllanthocin acid is isolated by chromatography.

Biologically active derivatives of phyllanthocin acid are made by coupling it with suitably protected sugars or other hydroxylated compounds by methods well known in the art [see Methods in Chemistry by R. L. Whistler and J. N. Bemiller (eds.), Academic Press, N.Y., 1972, Vol. 6, or The Carbohydrates: Chemistry and Biochemistry by W. Pigman, Academic Press, NY, 1981].

Derivatives of phyllanthocin acid are used for the same purposes as phyllanthoside and phyllanthostatins 1, 2 and 3.

In like manner, a related set of derivatives having the aglycone moiety of phyllanthostatin 3 is obtained by starting with phyllanthostatin 3 in place of phyllanthoside in the above procedure.

The phyllanthostatins and phyllanthoside have free hydroxyl groups available for derivatization. Thus, acyl esters of these compounds can also be prepared by methods well known to those skilled in the art. Acyl derivatives of the phyllanthostatins can be used for the same biological purposes as the parent conpunds.

Acids which can be used in the acylation of a phyllanthostatin include:

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are:
mono-, di-, and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
malic acid;
citric acid; isocitric acid;
6-methylsalicylic acid;
mandelic acid;
levulinic acid;
pyruvic acid;
glycine;
alamine;
valine;
isoleucine;
leucine;
phenylalanine;
proline;
serine;
theonine;
tyrosine;
hydroxyproline;
ornithine;
lysine;
arginine;
histidine;
hydroxylysine;
phenylglycine;
p-aminobenzoic acid;
m-aminobenzoic acid;
anthranilic acid;
aspartic acid;
glutamic acid;
aminoadipic acid;
glutamine;
asparagine;
and the like.

STRUCTURE DETERMINATION

The complete structures of phyllanthostatin 1 and phyllanthoside were deduced by interpreting the $^{13}$C NMR (22.63 MHz, CDCl$_3$), $^1$H NMR (400 MHz, CDCl$_3$) and EI high resolution and FD mass spectra. Although the structure of phyllanthoside was not previously known, Kupchan and co-workers reported [Kupchan, S. M., supra] structural studies of two degradation products which proved very useful in the present study. Methanolysis of phyllanthoside gave an aglycone methyl ester, phyllanthocin (determined by X-ray crystallographic analysis) and a disaccharide, $C_{12}H_{22}O_9$. Acid hydrolysis of the disaccharide yielded 6-deoxy-D-glucose and spectral evidence suggested that the disaccharide portion contained two acetate groups.

Examination of the $^1$H and $^{13}$C NMR results for phyllanthostatin 1 and phyllanthoside indicated that these potent antineoplastic plant constituents have identical aglycones and differ only in the disaccharide portion. Both glycosides afforded identical peracetates [mp 122°–126° C., $[\alpha]_D^{24}+26.3°$ (c 1.1, CHCl$_3$)] and were readily interconverted via an acetyl shift upon standing at room temperature for periods exceeding 24 hr in 90% aqueous ethanol. Thus, phyllanthostatin and phyllanthoside differ only in the location of one acetyl group on the disaccharide unit and consist of aglycone phyllanthocin acid joined via an ester linkage to a diacetylated 6-deoxy-D-glucose disaccharide. In addition, the $^3J_{HH}$ coupling constants of ~8 Hz measured for both anomeric protons of phyllanthostatin 1 and phyllanthoside indicated β-linkages at the anomeric centers. At this point only the location of the three 6-deoxy-D-glucose ester groups and position of the disaccharide linkage of phyllanthostatin 1 and phyllanthoside remained to be solved.

The $^1$H NMR spectrum of phyllanthoside exhibited two 6-deoxy-D-glucose ring proton resonances at δ4.78 and 4.90 ppm. The ca 1 ppm downfield shift of these resonances from the usual positions for such protons clearly indicated attachment to carbon atoms bearing ester groups [Hall, L. D., Advan. Carbohyd. Chem., 19, 51 (1964)] and $^1$H NMR decoupling studies revealed that these two ester linkages were at S-3 and S-3'. The $^{13}$C and $^1$H NMR results showed that the third ester linkage was at S-1 (S-1: $^{13}$C, 92.06; $^1$H, 5.50, d, J=8.1 Hz; S-1': $^{13}$C, 103.84; $^1$H, 4.00, d, J=7.8 Hz). Similar studies of phyllanthostatin 1 indicated that the ester linkages were at S-1, S-4 and S-3'. Because chemical (acetylation) evidence suggested that phyllanthostatin 1 and phyllanthoside differed only in the location of an acetate group, the ester at S-3 in phyllanthoside and S-4 in phyllanthostatin 1 must be acetate. Furthermore, treatment of phyllanthoside with cellulase in an acetate buffer (pH 5.0) yielded a monoacetyl derivative. Here $^1$H NMR studies of this derivative showed that the S-3' proton resonance was shifted upfield ca 1 ppm, whereas resonances for the aglycone and the other glucose protons remained essentially unchanged. Accordingly, the second acetate group resides at S-3' in both phyllanthostatin 1 and phyllanthoside and the aglycone must be linked to the disaccharide at S-1.

The final structural question concerned the nature of the disaccharide linkage. Because carbon atoms S-1 and S-3 in phyllanthoside and S-1 and S-4 in phyllanthostatin bear ester groups, the 6-deoxy-D-glucose units must, by elimination, be linked 1→2. This rather unusual linkage was confirmed by the following experiments. Methanolysis (0.1 M sodium methoxide in methanol) of phyllanthoside gave the methyl ester of phyllanthocin (FIG. 1) and disaccharide 2: mp 217°–219° C.; $[\alpha]_D^{26}$ −3.3° (c, 1.51, H$_2$O); $^1$H NMR (100 MHz, D$_2$O) $\delta$1.27 and 1.31 (6H, d, J=.Hz, 6,6'-CH$_3$), 3.06–4.12 (9H, m), 4.67 (d, J=8 Hz), 5.4 (d, J=4 Hz) ppm. [Kupchan, S. M., supra] Acetylation (acetic anhydride in pyridine) yielded a peracetate whose $^1$H NMR spectrum featured two methyl group doublets at $\delta$1.18 and 1.22, acetate methyl resonances at 2.00–2.20, a three-proton multiplet at 3.40–4.05, a group of resonances from 4.55–5.6, and an $\alpha$-anomeric proton ($^3$JHH=3 Hz) at 6.29 ppm. The resonance at 6.29 ppm was assigned to S-1. The lowfield resonances at 4.55–5.6 ppm were attributed to S-1' plus the protons of the acetate-bearing ring carbon atoms which experienced an expected downfield shift, relative to the parent disaccharide. The three protons appearing at 3.40–4.05 ppm correspond to S-5, S-5', and the proton on the carbon involved in the anomeric linkage to the second sugar. Proton decoupling experiments, showed resonances at 3.55 and 3.93 ppm which belong to S-5 and S-5' and a doublet of doublets at 3.90 coupled to the resonance at 6.29 ppm which must arise from S-2. Therefore, the anomeric linkage at S-2 was confirmed and the phyllanthostatin 1 and phyllanthoside structural assignments were completed.

Comparison of the spectral data recorded for phyllanthostatin 2 and phyllanthoside) indicated a difference in one of the disaccharide 6-deoxy-D-glucose units. The NMR signal arising from one of the 6-deoxy-D-glucose methyl groups in phyllanthoside ($^1$H-NMR: d at 1.28 ppm; $^{13}$C NMR 17.48 ppm) was replaced by a signal due to a CH$_2$OH group ($^1$H NMR: dd at 3.83 ppm; $^{13}$C NMR 61.90 ppm appearing as a triplet in the off-resonance decoupled spectrum) in 1c. When $^1$H NMR decoupling studies revealed that the CH$_2$OH moiety was located at position S-5, it was apparent that one of the 6-deoxy-D-glucose units of phyllanthoside was replaced by glucose. Therefore the structure shown in the Chart was assigned to phyllanthostatin 2.

Phyllanthostatin 3 was found to differ significantly from phyllanthoside in the aglycone moiety but possesses an identical disaccharide portion. The AB quartet at 2.92 and 2.95 ppm in the $^1$H NMR spectrum of phyllanthoside due to the epoxide methylene protons was replaced by two doubled doublets at 3.51 and 4.01 ppm in the spectrum of phyllanthostatin 3. Analogous marked differences were apparent in the $^{13}$C NMR spectra. The signals due to C-7 and C-14 (71.00 and 50.01 ppm in 1B) of the phyllanthoside epoxide occurred instead at 85.27 and 66.61 ppm respectively in phyllanthostatin 3. Less pronounced changes were observed in the chemical shift values of C-1, C-6, C-8 and C-9. These observations, together with mass spectral and elemental analytical data established that phyllanthostatin 3 was a vicinal 7,14-diol counterpart of the 7,14-epoxide phyllanthoside. Therefore the structure shown in the Chart was assigned to phyllanthostatin 3.

| | Antineoplastic Activity[d] Mouse Tumor System | | | |
|---|---|---|---|---|
| | B$_{16}$ melanoma[a] | | P$_{388}$ leukemia[a] | |
| Compound | optimal dose in mg/kg/ injection[b] | life span in percent of controls[c] | optimal dose in mg/kg/ injection[b] | life span in percent of controls[c] |
| Phyllanthoside | 16 | 190 | 8 | 149 |
| Phyllanthostatin 1 | 24 | 205 | 50 | 148 |
| | | | 7 | 152 |
| Phyllanthostatin 2 | | | 10 | 141 |
| Phyllanthostatin 3 | | | 80 | 141 |

[a]tumors were inoculated intraperitoneally (i.p.)
[b]compounds were administered i.p. every day for 9 days starting on the first day after tumor inoculation.
[c]Calculated from median survival times; Nos. in parentheses = No. of cures/total No. of mice in group. Cured mice survive for at least 60 days.
[d]A description of the antitumor tests appears in the reference by R. I. Geran, N. H. Greenberg, M. M. MacDonald, A. M. Schumacher and B. J. Abbott, Cancer Chemother. Rep. Part 3, Vol. 3(2): 1–103 (1972).

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as in adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or by dry powder for insufflation.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as co-solvents and wetting agents, as may be necessary or desirable.

The term "unit dosage form" as used in the specification and claims refers to physically discrete units suitable as unitary dosages for animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as anti-viral or anti-neoplastic agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

COMPOSITION EXAMPLE 1

Hard-Gelatin Capsules

One thousand two-piece hard gelatin capsules for oral use, each capsule containing 200 mg of a phyllanthostatin are prepared from the following types and amounts of ingredients:

a phyllanthostatin, micronized—200 gm
Corn Starch—20 gm
Talc—20 gm
Magnesium stearate—2 gm The phyllanthostatin, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a phyllanthostatin in 50, 250 and 500 mg amounts by substituting 50 gm, 250 l gm and 500 gm of a phyllanthostatin for the 200 gm used above.

COMPOSITION EXAMPLE 2

Soft Gelatin Capsules

One-piece soft gelatin capsules for oral use, each containing 200 mg of a phyllanthostatin (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION EXAMPLE 3

Tablets

One thousand tablets, each containing 200 mg of a phyllanthostatin are prepared from the following types and amounts of ingredients:

A phyllanthostatin, micronized—200 gm

Lactose—300 gm
Corn starch—50 gm
Magnesium stearate—4 gm
Light liquid petrolatum—5 gm The phyllanthostatin finely divided by means of an air micronizer, is added to the other ingredients and then thoroughly mixed and slugged. The slugs are broken down by forcing through a Number Sixteen screen. The resulting granules are then compressed into tablets, each tablet containing 200 mg of the phyllanthostatin.

The foregoing tablets are useful for treating a neoplastic disease by the oral administration of one or two tablets one to four times a day.

Using the procedure above, tablets are similarly prepared containing a phyllanthostatin in 250 mg and 100 mg amounts by substituting 250 gm and 100 gm of a phyllanthostatin for the 200 gm used above.

COMPOSITION EXAMPLE 4

Oral Suspension

One thousand ml of an aqueous suspension for oral use, containing in each teaspoonful (5 ml) dose, 50 mg of a phyllanthostatin, is prepared from the following types and amounts of ingredients:
A phyllanthostatin, micronized—10 gm
Citric acid—2 gm
Benzoic acid—1 gm
Sucrose—790 gm
Tragacanth—5 gm
Lemon Oil—2 gm
Deionized water, q.s. 1000 ml.

The citric acid, benzoic acid, sucrose, tragacanth and lemon oil are dispersed in sufficient water to make 850 ml of suspension. The phyllanthostatin, finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION EXAMPLE 5

A sterile aqueous suspension for parenteral injection, containing in 1 ml 300 mg of a phyllanthostatin for treating a neoplastic disease, is prepared from the following types and amounts of ingredients:
A phyllanthostatin, micronized—30 gm
Polysorbate 80—5 gm
Methylparaben—2.5 gm
Propylparaben—0.17 gm
Water for injection, q.s. 1000 ml.

All the ingredients, except the phyllanthostatin, are dissolved in the water and the solution sterilized by filtration. To the sterile solution is added the sterilized phyllanthostatin, finely divided by means of an air micronizer, and the final suspension is filled into sterile vials and the vials sealed.

The composition so prepared is useful for treating a neoplastic disease at a dose of 1 milliliter (1 M) three times a day.

COMPOSITION EXAMPLE 6

Suppository, Rectal and Vaginal

One thousand suppositories, each weighing 2.5 gm and containing 200 mg of a phyllanthostatin are prepared from the following types and amounts of ingredients:

A phyllanthostatin, micronized—15 gm
Propylene glycol—150 gm
Polyethylene glycol #4000, q.s. 2,500 gm The phyllanthostatin is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION EXAMPLE 7

Intranasal Suspension

One thousand ml of a sterile aqueous suspension for intranasal instillation, containing in each ml 200 mg of a phyllanthostatin, is prepared from the following types and amounts of ingredients:
A phyllanthostatin, micronized—15 gm
Polysorbate 80—5 gm
Methylparaben—2.5 gm
Propylparaben—0.17 gm
Deionized water, q.s. 1000 ml.

All the ingredients, except the phyllanthostatin, are dissolved in the water and the solution sterilized by filtration. To the sterile solution is added the sterilized phyllanthostatin, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present, as shown in Examples 12–14 in the undiluted pure form for use locally about the cutis, intranasally, pharyngolaryngeally, bronchially, broncholially or orally.

COMPOSITION EXAMPLE 8

Powder

Five grams of a phyllanthostatin in bulk form is finely divided by means of an air micronizer. The micronized powder is placed in a shaker-type container.

The foregoing composition is useful for treating a neoplastic disease, at localized sites by applying the powder one to four times per day.

COMPOSITION EXAMPLE 9

Oral Powder

One hundred grams of a phyllanthostatin in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION EXAMPLE 10

Insufflation

One hundred grams of a phyllanthostatin in bulk form is finely divided by means of an air micronizer.

The foregoing composition is useful for treating a neoplastic disease, by the inhalation of 300 mg one to four times per day.

COMPOSITION EXAMPLE 11

Hard Gelatin Capsules

One hundred two-piece hard gelatin capsules for oral use, each capsule containing 200 mg of a phyllanthostatin.

The phyllanthostatin is finely divided by means of an air micronizer and encapsulated in the usual manner.

The foregoing capsules are useful for treating a neoplastic disease, by the oral administration of one or two capsules one to four times a day.

Using the procedure above, capsules are similarly prepared containing phyllanthostatin in 50, 250 and 500 mg amounts by substituting 50 gm, 250 gm and 500 gm of a phyllanthostatin for the 200 gm used above.

CHROMATOGRAPHIC AND ANALYTICAL METHODS

Supplies and Equipment

All solvents were redistilled. Adsorption column chromatography was performed with silica gel 60 (70–230 mesh) or with prepacked silica gel 60 columns sizes A, B and C, both from E. Merck, Darmstadt. Reverse phase column chromatography was performed with RP-2 silanized silica gel 60 (70–230 mesh) (prewashed with methylene chloride and methanol) from E. Merck, Darmstadt, and gel filtration chromatography with Sephadex LH-20 (particle size 25–100µ) supplied by Sigma Chemical Co. Thin-layer chromatography was performed with silica gel GHLF Uniplates (layer thickness 0.25 mm) supplied by Analtech Inc. and precoated RP-2 silanized silica gel 60 F254 plates (layer thickness 0.25 mm) from E. Merck. Visualization of the plates was conducted with anisaldehyde or ceric sulfate spray reagents, or by exposure to ultraviolet light. In all cases, column chromatography was performed after equilibration of the sorbent or gel with the initial eluting solvent and the fractionation was monitored and partially automated using a Gilson Model HM UV-Vis Holochrome and Gilson Model FC-220K and Micro Fractionators. The purity of all products was determined by high performance liquid chromatography on a µ-Porasil column (30 cm×4 mm) with methylene chloride-methanolwater (97-3.0-0.2) as eluant, using a Waters Liquid Chromatograph ALC 2000 Series with a Model 440 Absorbance detector ($\lambda$, 254 nm). Melting points are uncorrected and were determined on a Kofler-type hot-stage apparatus, and optical rotations were measured on a Perkin-Elmer Model 24-1 Automatic Polarimeter. Ultraviolet spectra were recorded on a Hewlett-Packard Model 8450A UV/VIS Spectrophotometer and infrared spectra on a Perkin Elmer Model 299 Spectrophotometer. $^1$H-NMR spectra (deuteriochloroform solution and tetramethylsilane internal standard) were recorded on a Bruker WH-400 and Varian XL-100 spectrometers and $^{13}$C-NMR spectra were measured at 22.63 MHz on a Bruker WH-90 spectrometer and are reported in ppm downfield from tetramethylsilane. Mass spectra were obtained using Varian MAT 731 and MAT 312 spectrometers. Elemental analyses were determined at the Spang Microanalytical Laboratory, Ann Arbor, Mich.

Acetylation of Phyllanthostatin 1 and Phyllanthoside to Give S-3,4,2′,3′,4′-Pentaacetyl Phyllanthoside Phyllanthoside (80 mg) was treated with pyridine (2 ml) and acetic anhydride (2 ml) and the mixture allowed to stand at 3° C. for 48 hr. Excess water was added and the flocculent precipitate centrifuged off. After washing the precipitate three times with water, methylene chloride was added, the solution dried ($Na_2SO_4$) and evaporated to give a glassy material (82 mg). Chromatography on silica gel-60 (Lobos A column) and elution with 1% methanol-methylene chloride gave the pentaacetate (55 mg) as an amorphous solid: mp 122°–126° C.; EI mass spectrum m/e 930 (M$^+$); $[\alpha]_D^{30}+31.8°$ (c 1.13, CHCl$_3$) ($[\alpha]_D^{24}+26.3°$); IR (KBr) $\nu_{max}$ 1756, 1707, 1636, 1450, 1376, 1246, 1216, 1174, 1124, 1074, 1052, 1034, 950, 905 and 767 cm$^{-1}$; $^1$H- and $^{13}$C-NMR.

Similar acetylation of phyllanthostatin 1 (40 mg) gave a pentaacetate (26 mg) which was shown to be identical to the pentaacetate formed from phyllanthoside by HPLC and comparison of infrared spectra.

Treatment of Phyllanthoside with Refluxing Methanol to Give S3,S3′-Didesacetylphyllanthoside Phyllanthoside (200 mg) in methanol (20 ml) was refluxed for 15 hr. Evaporation of the solvent in vacuo gave material (198 mg) which was chromatographed on silica gel-60 (Lobos A column) using methylene chloride-methanol-water (90/10/0.2) as eluant. Elution between volumes 40–60 ml gave S3,S3′-didesacetylphyllanthoside (193 mg) as an amorphous solid; mp 133°–135°; FD mass spectrum; $[\alpha]_D^{26}+16.28°$ (c, 0.86, CHCl$_3$); IR (KBr) $\nu_{max}$ 3440, 1753, 1711, 1640, 1452, 1310, 1280, 1208, 1170, 1123, 1073, 1012, 990, 950, 908, 771 and 732 cm$^{-1}$; $^1$H and $^{13}$C-NMR.

Anal. Calcd. for $C_{36}H_{48}O_{15}\cdot H_2O$: C, 58.54; H, 6.77. Found: C, 58.81; H, 6.62%.

Methanolysis of Phyllanthoside to Give Phyllanthocin (2 g) and 2-O-($\beta$-6-deoxy-D-glucopyranosyl)-6-deoxy-D-glucopyranoside Phyllanthoside (310; 0.39 mmol) was stirred at room temperature with 0.1 M sodium methoxide (15 ml) for 30 min. The mixture was neutralized by the dropwise addition of 1 M hydrochloric acid, and concentrated in vacuo to a small volume, and partitioned between water (20 ml) and methylene chloride (3×20 ml). Evaporation of the organic phase gave material (180 mg) which was chromatographed on silica gel-60 (Lobos A column). Elution with methylene chloride gave phyllanthocin (161 mg; 2 g) which was recrystallized from ether-hexane to give pure crystalline material: mp 120°–121° C.; $[\alpha]_D^{33}+23.81°$ (c, 1.26, CHCl$_3$); $[\alpha]_D^{24}+25.2°$; IR (KBr) $\nu_{max}$ 1728, 1708, 1642, 1628, 1497, 1450, 1435, 1385, 1362, 1340, 1325, 1308, 1297, 1278, 1252, 1204, 1170, 1145, 1121, 1072, 1058, 1021, 991, 981, 950, 902, 870, 842, 815, 770, 710, 690, 680 and 620 cm$^{-1}$; $^1$H-NMR (100 mHz) (CDCl$_3$) $\delta$0.88 (3H, d, J=7 Hz), 2.91 (1H, d, J=5 Hz), 3.00 (1H, d, J=5H$_2$), 3.30 (3H, s), 3.47 (1H, dd, J=11 and 5 Hz), 4.05 (1H, t, J=11 Hz), 4.44 (1H, m), 5.13 (1H, m), 6.54 (1H, d, J=16 Hz), 7.4–7.7 (5H, m), 7.82 (1H, d, J=16 Hz). The above spectral data corresponds closely to that published for phyllanthocin.

The aqueous phase was treated with freshly washed Amberlite MB-3 resin until the supernatant liquid was free of chloride ion. Lyophilization of the filtrate gave 2-O-($\beta$-6-deoxy-D-glucopyranosyl)-6-deoxy-D- glucopyranoside (84 mg) as a white solid: mp 218–220; $[\alpha]_D^{26} -3.3°$ (c, 1.51, H$_2$O); IR (KBr) $\nu_{max}$ 3381, 1445, 1380, 1357, 1248, 1180, 1150, 1125, 1062, 1010, 986, 935, 922, 896, 836 and 772 cm$^{-1}$; $^1$H-NMR (100 MHz D$_2$O) δ1.27, 1.31 (3H each, d, J=6 Hz, 56- and 56′-CH$_3$), 3.06–4.12 (9H, MO, 4.67 (d, J=8 Hz), 5.4 (d, J=4 Hz) ppm; $^{13}$C-NMR (D$_2$O) δ104.86 and 103.95 (cl′), 95.67 (β-Cl), 92.74 (α-Cl), 83.74 (β-C2), 81.92 (α-C2), 76.43, 76.17, 76.01, 75.78, 75.00, 74.68, 73.12, 72.95, 72.86, 72.63, 68.14, 17.81 (6- and 6′-CH$_3$) ppm.

Anal. Calcd. for C$_{12}$H$_{22}$O$_9$: C, 46.45; H, 7.10. Found: C, 45.83; H, 7.13%.

Acetylation of the above disaccharide (65 mg) with acetic anhydride (2 ml) and pyridine (2 ml) at room temperature for 48 hr, followed by addition of excess water, gave a white solid which was filtered off and thoroughly washed with water. Recrystallization of the solid from acetone-hexane gave α-2-O-(β-6-deoxy-D-glucopyranosyl)-6-deoxy-D-glucopyranose hexaacetate: mp 224°–226°; EI mass spectrum m/e 562 (M$^+$), 561 (M$^+$-H), 503 (M$^+$-O$_2$CCH$_3$); $[\alpha]_D^{26} +71.08°$ (c 0.83, CHCl$_3$) IR (KBr) $\nu_{max}$ 1755, 1435, 1380, 1250, 1222, 1176, 1128, 1067, 1031, 1010, 944, 922, 909 and 890 cm$^{-1}$; $^1$H-NMR (100 MHz; CDCl$_3$) δ1.18 and 1.22 (3H each, d, J=6 Hz, 56- and 56′-CH$_3$), 2.00, 2.02, 2.05, 2.07, 2.09 (15H, all s, 5 O$_2$CCH$_3$), 2.18 (3H, s, O$_2$CCH$_3$), 3.55 and 3.93 (1H each, m, 55- and 55′-H), 3.90 (1H, dd, J=11 and 4 Hz 52-H), 4.55–5.60 (6H, m, 51′- and 5 CHO$_2$CCH$_3$), 6.29 (1H, d, J=3 Jz 51-H) ppm; $^{13}$C-NMR δ170.37, 169.85 (2c), 169.53 (2c), 169.14 (6×CH$_3$C), 100.99 (Cl′), 90.47 (Cl), 75.62, 73.54, 73.18, 72.82, 71.62 (2c), 70.22, 67.30, 20.89, (2c), 20.83, 20.63 (2c) and 120.41 (6×CH$_3$CO$_2$), 17.35 and 17.22 (6- and 6′-CH$_3$) ppm.

Anal. Calcd. for C$_{24}$H$_{34}$O$_{15}$: C, 51.24; H, 6.05. Found: C, 50.84; H, 5.96%.

Enzymatic Hydrolysis of Phyllanthostatin 1 to Give S3′-Monodesacetyl Phyllanthostatin 1

Phyllanthostatin 1 (82 mg; 0.1 mmol) in acetate buffer (pH=5.0; 80 ml) was treated with cellulase (Sigma Chemical Co.) (105 mg; 150 units) as reported for phyllanthoside to give material (47 mg) which was chromatographed on silica gel-60 (Lobos A column) using methylene chloride-methanol-water (93/7/0.2) as eluant. Elution between volumes 85–100 ml gave S3′-monodesacetylphyllanthostatin 1 (21 mg) as an amorphous solid: mp 127°–132°; FD mass spectrum m/e $[\alpha]_D^{26} +20.83°$ (c, 0.72, CHCl$_3$); IR (KBr) $\nu_{max}$ 3440, 1750, 1710, 1640, 1452, 1377, 1310, 1280, 1235, 1170, 1075, 1020, 992, 950, 907 and 771 cm$^{-1}$; $^1$H-NMR.

CHART

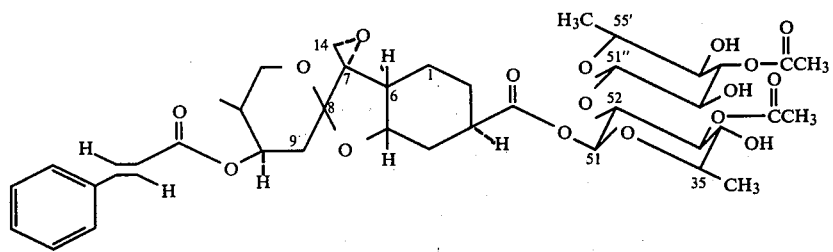

Phyllanthoside

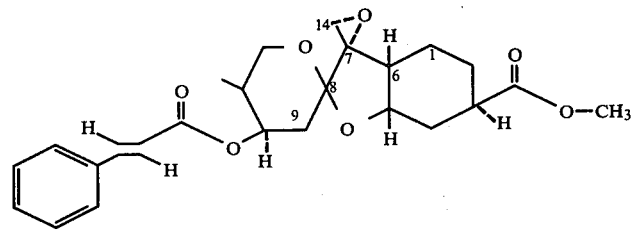

Phyllanthocin

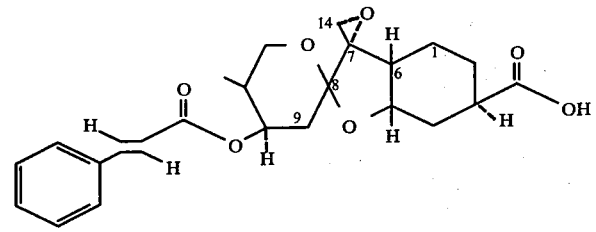

Phyllanthocin acid

CHART

—continued

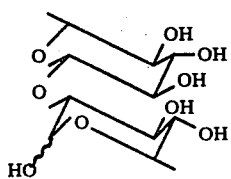

Disaccharide 2

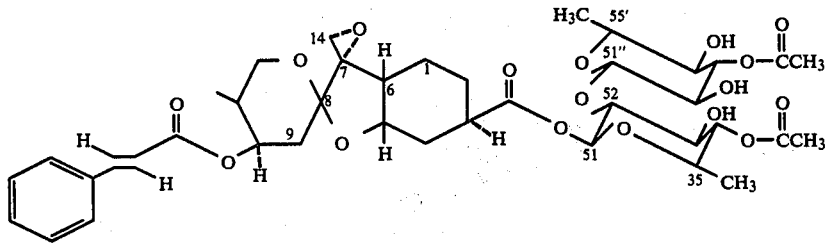

Phyllanthostatin 1

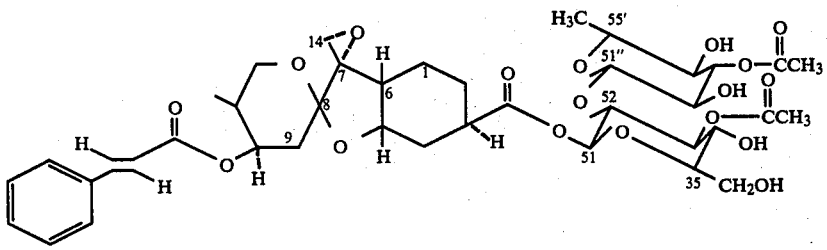

Phyllanthostatin 2

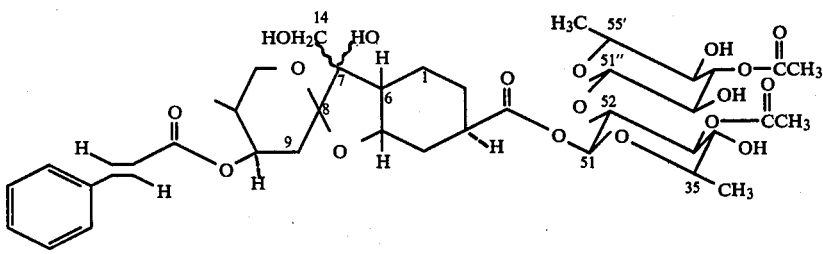

Phyllanthostatin 3

I claim:
1. Phyllanthostatin 1 which has the following characteristics:
Melting point—125°–126° C.;
Field desorption mass spectrum—m/e 805 (M$^+$+H);
Optical rotation—[α]$_D^{26}$ −3.6° (c 0.83, CHCl$_3$);
Ultra violet absorption spectrum—$\nu_{max}^{MeOH}$ nm (log ε) 216 (4.19), 222 (4.12) and 277 (4.29);
Infrared absorption spectrum—(KBr) $\nu_{max}$ 3450, 1755, 1740, 1710, 1640, 1452, 1380, 1310, 1245, 1170, 1075 and 770 cm$^{-1}$;
and which can be shown by the following structural formula:

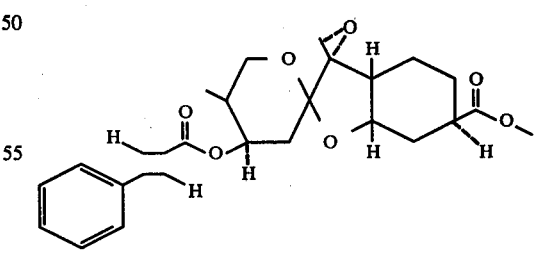

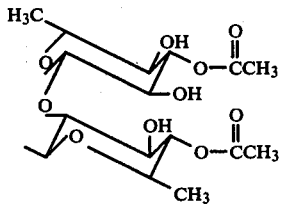

2. Phyllanthostatin 2 which has the following characteristics:
Melting point—134°–136° C.;
Field desorption mass spectrum—m/e 821 (M+ +H);
Optical rotation—$[\alpha]_D^{24}$ +9.33° (C=0.75, CHCl$_3$);
Ultra violet absorption spectrum—$\lambda_{max}^{MeOH}$ nm (log ε) 216 (4.28), 222 (4.21) and 278 (4.38);
Infrared absorption spectrum—(KBr) $\nu_{max}$ 3470, 1750, 1730, 1710, 1640, 1452, 1380, 1311, 1257, 1171, 1075 and 770 cm$^{-1}$;
and which can be shown by the following structural formula:

3. Phyllanthostatin 3 which has the following characteristics:
Melting point—126°–130° C.;
Optical Rotation—$[\alpha]_D^{26° C.}$ (C, 0.76, CHCl$_3$)= +15.7°;
Field desorption mass spectrum—m/e 323 (M+ +H);
Ultra violet absorption spectrum—$\lambda_{max}^{MeOH}$ nm (log ε) 216 (4.25), 222 (4.18) and 278 (4.35);
Infrared absorption spectrum—(KBr) $\nu_{max}$ 3450, 1755, 1730, 1700, 1640, 1455, 1380, 1311, 1258, 1175, 1070 and 772 cm$^{-1}$;
and which can be shown by the following structural formula:

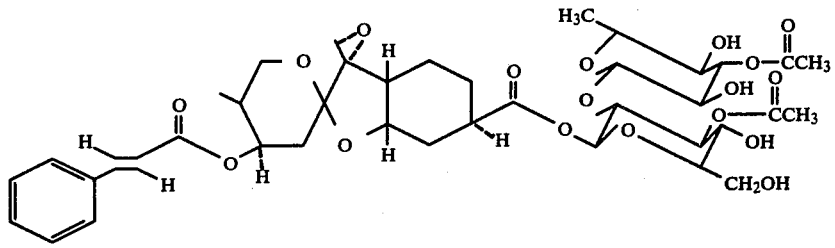

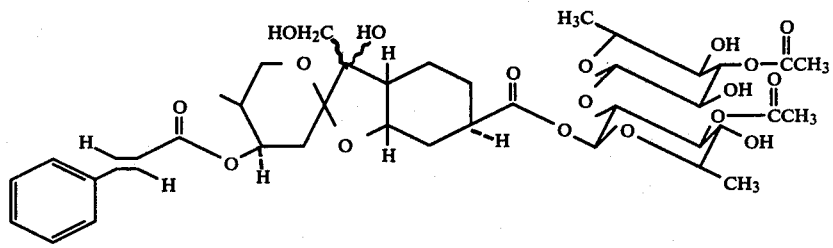

* * * * *

UNITED STATES PATENT OFFICE
CERTIFICATE OF CORRECTION

Patent No. 4,388,457　　　　　　　　　　Dated June 14, 1983

Inventor(s) George R. Pettit

It is certified that error appears in the above-identified patent and that said Letters Patent are hereby corrected as shown below:

On cover page, 8th line of Abstract "malanoma" should read --melanoma--

Column 1, line 8 "Ol in" should read --Olin--

Column 1, line 66 "2-2.5 cm." should read --2-4.5 cm.--

Column 2, line 1 "axially" should read --axillary--

Column 4, line 48 "conpunds" should read --compounds--

Column 6, line 3 "theonine" should read --threonine--

Column 10, line 47 "250 lgm" should read --250 gm--

Signed and Sealed this

Sixteenth Day of August 1983

[SEAL]

Attest:

GERALD J. MOSSINGHOFF

*Attesting Officer*　　*Commissioner of Patents and Trademarks*